United States Patent [19]

Sugihara et al.

[11] 4,010,202
[45] Mar. 1, 1977

[54] 5,6-DIHYDROXY AMINOTETRALOL COMPOUNDS

[75] Inventors: Hirosada Sugihara; Masazumi Watanabe, both of Osaka; Michio Motohashi, Kobe; Masao Nishikawa, Kyoto; Yasushi Sanno, Osaka, all of Japan

[73] Assignee: Takeda Chemical Industries, Ltd., Osaka, Japan

[22] Filed: Mar. 4, 1975

[21] Appl. No.: 555,128

[30] Foreign Application Priority Data

Apr. 25, 1974  Japan .............................. 49-47211

[52] U.S. Cl. .............. 260/573; 260/256.4 R; 260/288 R; 260/293.87; 260/296 R; 260/306.8 R; 260/307 R; 260/326.15; 260/329 AM; 260/333; 260/501.1; 260/501.18; 260/501.19; 260/501.21; 260/559 A; 260/566 R; 260/570.8 R; 260/571; 260/574; 424/330

[51] Int. Cl.² .................. C07C 91/06; C07C 91/42; C07C 93/14; A61K 31/135

[58] Field of Search ................ 260/571, 573, 574; 424/330

[56] References Cited

UNITED STATES PATENTS

| | | | |
|---|---|---|---|
| 3,534,055 | 10/1970 | Gittos et al. | 260/574 X |
| 3,579,582 | 5/1971 | Symon | 260/574 |
| 3,751,420 | 8/1973 | Hauck et al. | 260/571 X |
| 3,930,022 | 12/1975 | Hauck et al. | 260/574 X |

OTHER PUBLICATIONS

Thrift, "J. Chem. Soc., C", pp. 288–293 (1967).
Chiemprasert et al., "Ann. Chem.", Band 685, pp. 141–148 (1965).

*Primary Examiner*—Daniel E. Wyman
*Assistant Examiner*—John J. Dell
*Attorney, Agent, or Firm*—Wenderoth, Lind & Ponack

[57] ABSTRACT

Novel aminotetralol compounds of the formula

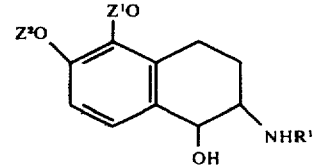

wherein $Z^1$ and $Z^2$ are hydrogen or an alkyl group and $R^1$ is a substituted acyclic hydrocarbon group or a cyclic hydrocarbon group, and their pharmaceutically acceptable salts, have excellent pharmacological activities such as strong bronchodilating activity or β-adrenergic blocking activity. They are useful as medicines, for example, for treatment of asthma or arrhythmia.

23 Claims, No Drawings

5,6-DIHYDROXY AMINOTETRALOL COMPOUNDS

This invention relates to novel aminotetralol compounds of the formula

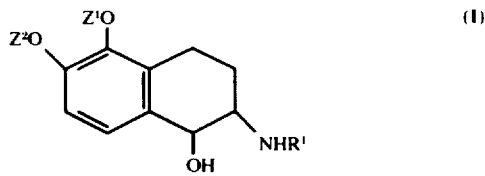

wherein $Z^1$ and $Z^2$ are hydrogen or an alkyl group and $R^1$ is a substituted acyclic hydrocarbon group or a cyclic hydrocarbon group, and their pharmaceutically acceptable salts which have excellent pharmacological activities such as strong bronchodilating activity or $\beta$-adrenergic blocking activity, and which are useful as medicines, for example, for treatment of asthma or arrhythmia.

As medicines for the treatment of asthma, isoproterenol and metaproterenol, both of which have a stimulating action of $\beta$-adrenergic receptors, have been widely employed. However, while isoproterenol has a bronchodilator action which is said to be associated with $\beta_2$-adrenergic receptors, it has potent side effects due to its strong cardiac stimulation which is said to be associated with $\beta_1$-adrenergic receptors; metaproterenol on the other hand has only moderate side effects of the above type but is decidedly inferior in bronchodilator activity. Therefore, neither of them has been thought to be satisfactory as a selective bronchodilator.

The above situation provided an impetus to our intensive research, which has led to success in synthesizing the novel compound (I), which has strong bronchodilator activity and, yet, has only moderate, or is substantially devoid of, side effects caused by $\beta_1$-adrenergic stimulation.

Thus, the principal object of the present invention is to provide the compound (I) and its pharmaceutically acceptable salts, which are useful as medicines for treatment of asthma or arrhythmia. Another object of the present invention is to provide a method for producing the novel and useful compound (I) and its pharmaceutically acceptable salts. Other objects will be made clear from the description and claims hereinafter.

Referring, now, to the formula (I), the alkyl group designated by symbols $Z^1$ and $Z^2$ may be straight or branched alkyl group and, advantageously a lower alkyl group, especially of up to six carbon atoms, such as methyl, ethyl, n-propyl, i-propyl, n-butyl, i-butyl, t-butyl, sec-butyl, n-pentyl, i-pentyl, t-pentyl, n-hexyl, i-hexyl and so on.

Referring to the formula (I), the substituted acyclic hydrocarbon group designated by symbol $R^1$ may be saturated or unsaturated and straight or branched. The acyclic hydrocarbon group is exemplified by an alkyl group, advantageously a lower alkyl group, especially of up to six carbon atoms (for example, methyl, ethyl, n-propyl, i-propyl, 1-methylpropyl, n-butyl, i-butyl, t-butyl, sec-butyl, n-pentyl, i-pentyl, t-pentyl, n-hexyl, i-hexyl, etc.), a lower alkenyl group especially of up to six carbon atoms, (for example, ethenyl, propenyl, butenyl, pentenyl, hexenyl, etc.), a lower alkynyl group, especially of up to six carbon atoms (for example, ethynyl, propynyl, butynyl, pentynyl, hexynyl, etc.) or the like. Among them more advantageous is a lower alkyl group branching at the $\alpha$-position to the amino group of the formula (I), especially of up to four carbon atoms, such as i-propyl, 1-methylpropyl and t-butyl. As the substituent or substituents of the aforementioned substituted acyclic hydrocarbon group, there may be mentioned, among others, a cycloalkyl group, advantageously of 3 to 7 membered-ring, for example, cyclopropyl, cyclobutyl, cyclopentyl, cyclohexyl, cycloheptyl, etc.), a cycloalkenyl group advantageously of 3 to 7 membered-ring (for example, 2-cyclopentenyl, 3-cyclohexenyl, etc.), a cycloalkylidene group advantageously of 3 to 6 membered-ring (for example, cyclohexylidene, cyclopentylidene, etc.), an aryl group (for example, phenyl, naphthyl, etc.), a heterocyclic group [for example, a heterocyclic group containing one oxygen (e.g. tetrahydrofuryl, tetrahydropyranyl, dihydropyranyl, furyl, etc.), a heterocyclic group containing one nitrogen (e.g. piperidinyl, pyridyl, indolyl, quinolyl, etc.), a heterocyclic group containing one sulfur (e.g. thienyl, tetrahydrothienyl, etc.), a heterocyclic group containing two or more and same or different heteroatoms (e.g. thiazolyl, pyrimidyl, oxazolyl, etc.), etc.], hydroxyl, a lower alkoxy group of 1 to 4 carbon atoms (for example, methoxy, ethoxy, propoxy, etc.), an aryloxy group (for example, phenoxy, naphthoxy, etc.), halogen (for example, chlorine, fluorine, bromine, iodine, etc.), esterified hydroxyl, an alkoxycarbonyl group, amino or substituted amino group (where the substituent or substituents may be alkyl, acyl or other groups), nitro, cyano and other groups. The aforementioned cycloalkyl, cycloalkenyl, aryl and heterocyclic groups may further contain appropriate substituent or substituents such as a lower alkyl group of 1 to 4 carbon atoms (for example, methyl, ethyl, propyl, etc.), hydroxyl, a lower alkoxy group of 1 to 4 carbon atoms (for example, methoxy, ethoxy, propoxy, etc.), halogen (for example, chlorine, bromine, iodine, fluorine). Among typical examples of the aforementioned substituted acyclic hydrocarbon group are cyclohexylmethyl, 1-cyclohexylethyl, 2-cyclopentylethyl, 3-cyclohexyl-1-methylpropyl, 4-methylcyclohexylmethyl, 1-cyclohexenylmethyl, 1-cyclopentenylmethyl, benzyl, 4-methoxybenzyl, 4-hydroxybenzyl, $\alpha$-methylbenzyl, 3,4-dimethoxybenzyl, $\alpha$-methylphenethyl, 4-methoxy-$\alpha$-methylphenethyl, 4-hydroxy-$\alpha$-methylphenethyl, 4-hydroxy-$\alpha$,$\alpha$-dimethylphenethyl, 4-methoxy-$\alpha$,$\alpha$-dimethylphenethyl, 4-chlorophenethyl, 3-phenylpropyl, phenethyl, 4-methoxyphenethyl, 2-phenylpropyl, $\alpha$,4-dimethylphenethyl, 1-methyl-2-cyclohexylidenethyl, tetrahydropyran-2-ylmethyl, 2,3-dihydropyran-2-ylmethyl, tetrahydrofuran-2-ylmethyl, 2-(furan-2-yl)-1-methylethyl, 2-thienylmethyl, piperidin-2-ylmethyl, 2-(2-indolyl)-1-methylethyl, 2-pyridylmethyl, 2-(2-thiazolyl)ethyl, 2-hydroxyethyl, 2-methoxyethyl, 3-ethoxy-1-methylpropyl, 6-methoxyhexyl, 1-methyl-2-phenoxyethyl, 2-fluoro-1-methylethyl, 2-ethoxycarbonylethyl, 2-aminoethyl, 3-dimethylaminopropyl, 3-morpholino-1-methylpropyl, 2-piperidino-1-methylethyl, nitromethyl, 2-cyano-1-methylethyl, styryl, 3-phenyl-2-propenyl and so on.

With reference to the formula (I), the cyclic hydrocarbon group denoted by $R^1$, is exemplified by a cycloalkyl group advantageously of 3 to 7 membered-ring (for example, cyclopropyl, cyclobutyl, cyclopentyl, cyclohexyl, cycloheptyl, etc.), a cycloalkenyl group, advantageously of 3 to 7 membered-ring (for example, cyclopentenyl, cyclohexenyl, etc.), an aryl group (for example, phenyl, naphthyl, etc.) and so on. Among them more advantageous is a cycloalkyl group of 3 to 7 membered-ring. These groups may contain, in optional positions, appropriate substituent or substituents such as the lower alkyl group, hydroxyl, lower alkoxy groups, halogen and other groups mentioned hereinbefore for the substituent or substituents of the cycloalkyl, cycloalkenyl, aryl and heterocyclic groups mentioned in connection with the substituted acyclic hydrocarbon group. Among typical examples of the aforesaid cyclic hydrocarbon group are cyclopropyl, cyclobutyl, cyclopentyl, cyclohexyl, cycloheptyl, methylcyclopropyl, 2-methylcyclobutyl, 3-methylcyclobutyl, 2,2-dimethylcyclobutyl, 3,3-dimethylcyclobutyl, 4-methylcyclohexyl, 4-hydroxycyclohexyl, 4-methoxycyclohexyl, 2-chlorocyclopentyl, 2-cyclohexenyl, 2-cyclopentenyl, phenyl, α-naphthyl, 4-chlorophenyl, 4-methoxyphenyl, 2-fluorophenyl, 4-hydroxyphenyl, 3,4-dimethoxyphenyl and so on.

The compound (I) of the present invention can be produced, for example, by reducing a compound of the formula

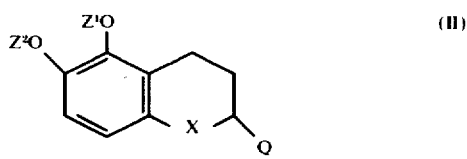

wherein $Z^1$ and $Z^2$ have the same meanings as defined hereinbefore, X is >C=O or >CH—OH and Q is a group of the formula —$NHR^1$ (wherein $R^1$ has the same meaning as defined hereinbefore), a group of the formula —$NHCOR^2$ (wherein $R^2$ is a substituted acyclic hydrocarbon group or, a cyclic hydrocarbon or heterocyclic group which may be substituted) or a group of the formula

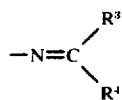

(wherein $R^3$ is hydrogen or an alkyl group and $R^4$ is a substituted acyclic hydrocarbon group or, a cyclic hydrocarbon or heterocyclic group which may be substituted, including a case where $R^3$ and $R^4$ form a ring group taken together with the adjacent carbon atom), with a proviso that when Q is a group of the formula —$NHR^1$, X is not >CH—OH.

Referring to the formula (II), in the case that Q is the group of the formula —$NHCOR^2$, the substituted acyclic hydrocarbon group of the cyclic hydrocarbon group which may be substituted, as designated by symbol $R^2$, is exemplified by the groups mentioned hereinbefore for $R^1$; the heterocyclic group which may be substituted, as also designated by $R^2$, is exemplified by the heterocyclic groups specifically mentioned in connection with the substituents on the acyclic hydrocarbon group $R^1$. In this case, a group of the formula —$NHCH_2R^2$ which is formed by the reduction of the group of the formula —$NHCOR^2$ corresponds to —$NHR^1$ in the formula (I).

Referring to the formula (II), in the case that Q is the group of the formula

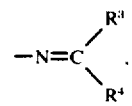

the alkyl group designated by symbol $R^3$ is exemplified by the alkyl group specifically mentioned in connection with $Z^1$ and $Z^2$ or $R^1$. The substituted acyclic hydrocarbon group or, the cyclic hydrocarbon or heterocyclic group which may be substituted, each as designated by symbol $R^4$, is exemplified by the corresponding groups specifically mentioned for $R^1$ and $R^2$. It should be noticed that $R^3$ and $R^4$ may form a ring group as taken together with the adjacent carbon atom; examples of said ring group include a cycloalkane group, advantageously of 3 to 7 membered-ring (e.g. cyclopropane, cyclobutane, cyclopentane, cyclohexane, cycloheptane, etc.), cycloalkene group, advantageously of 3 to 7 membered-ring (e.g. cyclopentene, cyclohexene, etc.) and so on. Among them more advantageous is a cycloalkane group of 3 to 7 membered-ring. In this case, a group of the formula

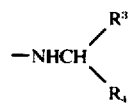

which is formed by the reduction of the group of the formula

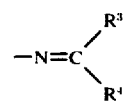

corresponds to —$NHR^1$ in the formula (I).

The reduction reaction in the above process is ordinary conducted by a reducing procedure suitably selected, according to the starting material then employed, from conventional ones such as given below; (1) catalytic reduction with platinum, palladium, rhodium, nickel, or the like by way of catalyst, (2) reduction by means of a metal hydride such as lithium aluminum hydride, lithium borohydride, lithium cyanoborohydride, sodium borohydride, sodium cyanoborohydride or the like, (3) Meerwein-Ponndorf-Verley reduction by means of aluminum alkoxide, e.g. aluminum isopropoxide, (4) reduction by means of metallic sodium, metallic magnesium or the like with, for example, alcohol, (5) reduction by means of zinc dust with base such as caustic alkali, (6) reduction by means of a metal such as iron or zinc with an acid such as hydrochloric acid or acetic acid, (7) electrolytic reduction. (8) reduction with the aid of reducing enzymes. It should be understood that, aside from the above procedures, any method can be employed that is able to reduce a carbonyl group to an alcohol or to saturate the double bond of the group of the formula

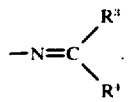

While the advantageous reaction temperature varies with starting materials and reduction procedures then employed, ordinarily it falls within the range of about −20 to about 100° C. This reaction is ordinarily carried out at atmospheric pressure but, if desired, it may be carried out at reduced or elevated pressure. The reduction is usually conducted in the presence of a suitable solvent. The solvent is of optional type, insofar as it is capable of dissolving, more or less, the starting material and will not adversely affect the reaction, such as water, an alcohol (e.g. methanol, ethanol, propanol, etc.), an ether (e.g. dimethyl ether, diethyl ether, methyl ethyl ether, tetrahydrofuran, dioxane, etc.) an ester (e.g. ethyl acetate, butyl acetate, etc.), a ketone (e.g. acetone, methyl ethyl ketone, etc.), an aromatic hydrocarbon (e.g. benzene, toluene, xylene, etc.), an organic acid (e.g. acetic acid, propionic acid, etc.) or a mixture of two or more thereof.

In the method of the present invention, starting materials of the formula (II) include various compounds, giving respectively corresponding object compounds (I). Thus, in accordance with the starting material and the desired object compound, the suitable reduction means and conditions are selected from those mentioned above.

For example, in a case that a compound (II) wherein X is >C=O and Q is the group of the formula —NHR¹ is employed as the starting material, i.e.

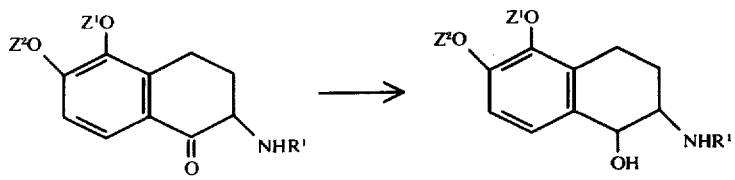

(wherein Z¹, Z² and R¹ have the same meanings as defined hereinbefore), when Z¹ and Z² are an alkyl group, the reduction means and conditions can optionally be selected from those mentioned before, and when both Z¹ and Z² are hydrogen, the catalytic reduction is advantageously used.

While, in a case that a compound (II) wherein Q is —NHCOR² is employed as the starting material, i.e.

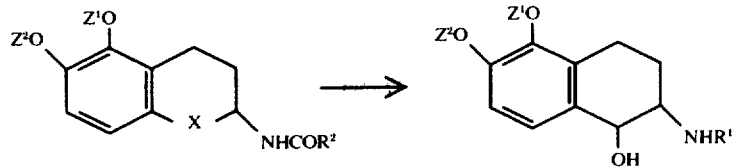

(wherein Z¹, Z², X, R¹ and R² have the same meanings as defined hereinbefore and, in this case, R¹ corresponds to —CH₂R²), the most typical means of the reduction is one using, for example, lithium aluminum hydride in the aforementioned procedure (2) under heating at about 40° to about 100° C.

In the case mentioned just above, when a compound (II) wherein X is >C=O and Q is —NHCOR² is employed as the starting material, a compound (II) wherein X is >CH—OH and Q is —NHCOR² may be intermediately produced.

In a case that a compound (II) wherein Q is

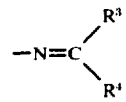

is employed as the starting meterial, i.e.

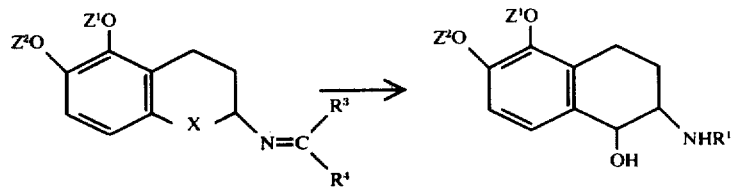

(wherein Z¹, Z², X, R¹, R³ and R⁴ have the same meanings as defined hereinbefore and, in this case, R¹ corresponds to

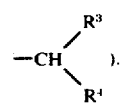

the reduction procedures (1) and (2) mentioned above are advantageously used.

This compound (II) wherein Q is

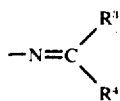

can be produced, for example, by reacting a compound of the formula

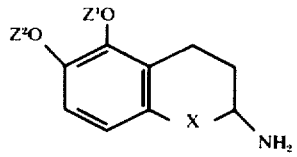

(wherein $Z^1$, $Z^2$ and X have the same meanings as defined hereinbefore) with a carbonyl compound of the formula

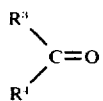

(wherein $R^3$ and $R^4$ have the same meanings as defined hereinbefore.) This reaction generally proceeds by merely mixing the compound (III) and the carbonyl compound (IV) in the solvent mentioned hereinbefore in connection with the reduction reaction but, if desired, the mixture may be heated or stood for sometimes to ensure the reaction, and various dehydrating or condensing agents may be employed in the reaction.

Therefore, in the case that the reduction reaction is carried out in the presence of the compound (III) and the carbonyl compound (IV), the amino group of the compound (III) first undergoes reaction with the carbonyl compound (IV) to produce the compound (II) wherein Q is

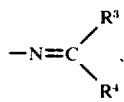

which, in turn, undergoes reduction to give the contemplated compound (I), i.e.

(wherein $Z^1$, $Z^2$, X, $R^1$, $R^3$ and $R^4$ have the same meanings as defined hereinbefore and, in this case $R^1$ corresponds to

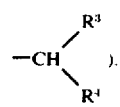

In the above reaction, it is possible to carry out the reaction using an excess of the carbonyl compound (IV) in place of the solvent.

In the method of this invention, when the aforementioned group $R^1$, $R^2$ or $R^4$ of the starting compound (II) is unsaturated, unsaturation other than aromatic unsaturation are more often than not reduced as well, and in the case of aromatic unsaturation, the contemplated compound (I) containing such an unsaturated group or one containing the corresponding saturated group can be selectively obtained by controlling the conditions of reduction.

The contemplated compound (I) of this invention can be easily isolated from the respective reaction mixtures by separation and purification procedures which are conventional per se, such as concentration, filtration, recrystallization, column chromatography and so on.

The compound (I) may occur in several stereo-isomers such as geometrical isomers and optical isomers due to the presence of some asymmetrical carbon atoms and, therefore, is commonly obtained as mixtures of such isomers.

If desired, an optional geometrical isomer (for example, trans-isomer, cis-isomer) can be obtained by suitable procedures such as (1) reduction with the use of the starting compound (II) wherein X is >CH—OH which has the same configuration as that of the contemplated compound (I), (2) stereospecific reduction (e.g. the compound (I) of trans-isomer is obtained by the reduction of the starting compound (II) wherein X is >C=O with the use of sodium borohydride), (3) isolation of the optional isomer from a mixture of isomers by using suitably selected procedures among the aforementioned separation and purification procedures such as recrystallization, column chromatography, and so on.

The racemic mixture may, if desired, be resolved by conventional procedures, for example by causing it to form a salt with an optically active acid or base or, alternatively, by physical adsorption on a porous ad-

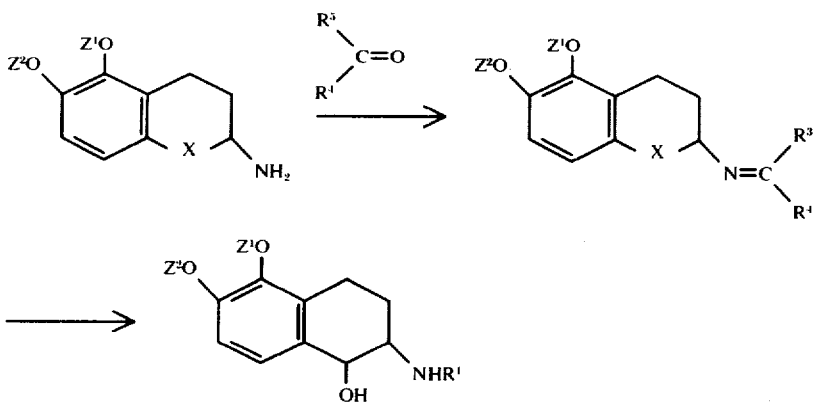

sorptive resin. It is to be understood that all such individual isomeric forms as well as their mixture are included in the scope of the present invention.

The contemplated compound (I) of this invention may also be isolated after it has been converted to pharmaceutically acceptable salts such as acid addition salts in the conventional manner; for example, an inorganic acid salt (such as hydrochloride, hydrobromide, sulfate, etc.), an organic acid salt (such as maleate, fumarate, tartrate, toluenesulfonate, naphthalenesulfonate, methanesulfonate, etc.).

The contemplated products of this invention thus obtained, i.e. the compound of the formula (I) and its pharmaceutically acceptable salts, have pharmacological activities such as the activity to stimulate or block β-adrenergic receptors, coronary vasodilator activity, analgetic activity and so on. Especially the activity to stimulate $\beta_2$-adrenergic receptors such as bronchodilating activity is noticable. Because of these useful properties of the compound (I) and its salts, they are of value in the therapy and prophylaxis of diseases such as asthma, arrhythmia, angina pectoris, migraine and so on.

In the pharmaceutical usage of any of the contemplated compound and its salts of this invention, it may be administered to mammals including human beings as it is or in admixture with a pharmaceutically acceptable carrier or carriers, orally or by other routes in such dosage forms as powders, granules, tablets, capsules, injections, inhalations, etc.

Pharmaceutical compositions containing one or more of the compound (I) or its salts can be prepared by conventional methods for the preparation of powders, granules, tablets, capsules, injections, inhalations and the like. The choice of carriers may be determined depending upon the route of administration, the solubility of the compound (I) and its salts, and so on.

While the proper dosage depends upon the particular disease and symptom to be dealt with, the route of administration and other conditions, advantageous dose levels in the therapy of asthma in adult humans are of the range of about 1 to 100 milligrams daily by the oral route, about 0.01 to 1 milligram per day intravenously or about 0.1 to 10 milligrams per dose by topical route in such dosage forms as nebulized products (aerosol inhalations).

Table 1, below, shows the relaxant action of typical compounds among the contemplated products of the present invention, on calf or guinea-pig isolated tracheal muscles in comparison with the corresponding action of isoproterenol, a known drug. The value given is relative to the value 100 for isoproterenol.

Table 1

| Compound | Isolated tracheal muscle relaxant activity* |
|---|---|
| 2-(3-Phenylpropylamino)-1,5,6-trihydroxy-1,2,3,4-tetrahydro-naphthalene hydrobromide | Ca. 200 (Calf) |
| 2-Cyclopentylamino-1,5,6-trihydroxy-1,2,3,4-tetrahydro-naphthalene hydrobromide | Ca. 190 (Calf) |
| 2-(4-hydroxy-α-methylphenethyl-amino)-1,5,6-trihydroxy-1,2,3,4-tetrahydronaphthalene fumarate | Ca. 600 (Guinea-pig) |

16 *Determined by the conventional method of E. J. Ariens appearing on Ciba Foundation Symposium, pp.253–263(1960).

The compound (I) of this invention is also of use as synthetic intermediates for the production of various drugs. For example, the compound (I) wherein $Z^1$ and $Z^2$ are an alkyl group can be easily converted to the corresponding compound (I) wherein both $Z^1$ and $Z^2$ are hydrogen by per se conventional methods such as hydrolysis.

The starting compound (II) wherein Q is

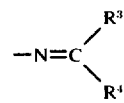

can be easily obtained by reacting the compound (III) with the carbonyl compound (IV) as mentioned hereinbefore.

The compound (III) wherein X is >C=O and $Z^1$ and $Z^2$ are each an alkyl group can be produced, for example by the method described in the literature [Journal of Medicinal Chemistry 12, 487(1969)] or a method based thereon, as set forth below.

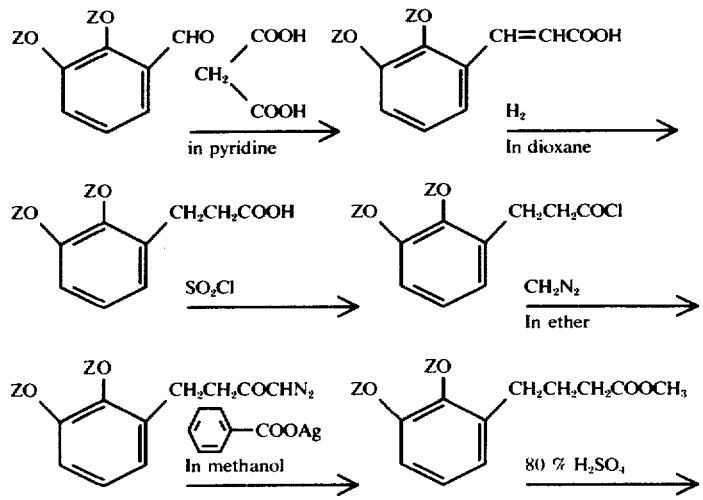

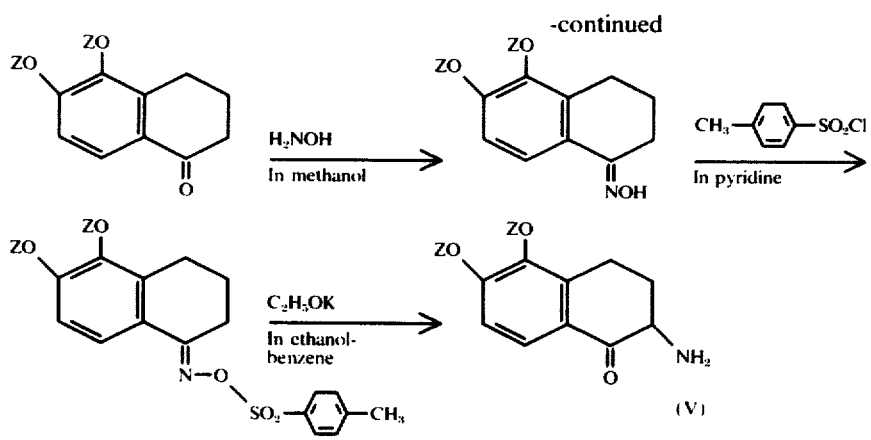

(wherein Z means an alkyl group)

[wherein Z means an alkyl group]

The compound (III) wherein X is >C=O and $Z^1$ and $Z^2$ are each hydrogen can be easily obtained, for example by hydrolyzing compound (V) with hydrobromic acid.

The compound (III) wherein X is >CH—OH can be produced by reducing the compound (III) wherein X is >C=O (for example, by reduction with sodium borohydride or by catalytic reduction).

The starting compound (II) wherein X is >C=O and Q is —NHCOR² can be obtained by acylating the aforementioned compound (V) or a hydrolyzate thereof in conventional manners (for example, by reaction with the corresponding acyl chloride in pyridine).

The starting compound (II) wherein X is >CH—OH and Q is —NHCOR² can be produced by reducing the aforementioned compound (II) wherein X is >C=O and Q is —NHCOR² (for example, by reduction with sodium borohydride or by catalytic reduction).

The starting compound (II) wherein X is >C=O and Q is —NHR¹ can each be produced, for example, (a) by reacting the compound (III) wherein X is >C=O or its N-acylated compound with a halide or a substituted sulfonyloxy derivative of the formula (VI) and, if necessary, by hydrolyzing the above reaction product, or (b) by reacting the same compound (III) with the carbonyl compound (IV) under reductive conditions, as shown below in reaction formulas:

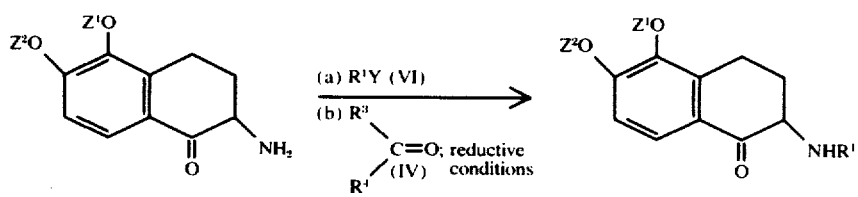

[wherein $Z^1$, $Z^2$, $R^1$, $R^3$ and $R^4$ have the meanings defined hereinbefore, provided that in the case of procedure (b), $R^1$ corresponds to

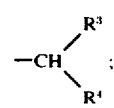

Y means halogen or a substituted sulfonyloxy group].

A further detailed explanation for the reactions (a) and (b) is as follows.

The reaction (a) may be carried out by processes as shown below in reaction formulas:

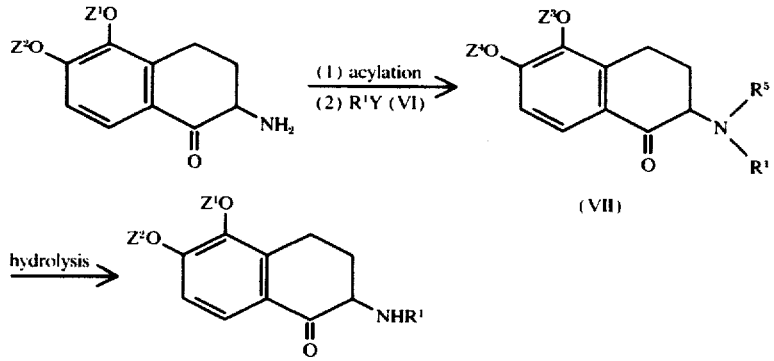

(wherein $Z^1$, $Z^2$, $R^1$ and Y have the meanings defined hereinbefore, $R^5$ is an acyl group, and $Z^3$ and $Z^4$ are hydrogen, an alkyl group defined as to $Z^1$ and $Z^2$, an acyl group having the same as $R^5$ or a protective group), Referring to the acylation reaction in the above reaction formulas, for the acylation of the starting compound, i.e. the compound (III) wherein X is >C=O, use may be made of any acylating agent that is capable of introducing the desired acyl group $R^5$ into the 2-amino group of the compound (III) wherein X is >C=O. As examples of said acylating agents, there may be mentioned carboxylic acids such as acetic acid, trifluoroacetic acid, propionic acid, etc.; carboxylic acid halides such as acetyl bromide, benzoyl chloride, trichloroacetyl chloride, ethyl chlorocarbonate, etc.; acid anhydrides such as acetic anhydride, trifluoroacetic anhydride, etc.; mixed acid anhydrides such as ethyl carbonate acetic anhydride, etc.; and sulfonic acid halides such as methanesulfonyl chloride, toluenesulfonyl chloride and so on.

The aforementioned acylation reaction is generally conducted in water, an organic solvent or a mixture of them, or using an excess of the acylating agent as a solvent. To hasten the reaction, it may be conducted in the concomitant presence of a base such as sodium hydroxide, potassium carbonate, pyridine, triethylamine or the like. As regards the proportion of acylating agent, one molecular equivalent is sufficient to consummate the contemplated acylation but, commonly, the acylating agent is used in a proportion of 2 to 10 equivalents or, when it is expected to act as a solvent as well, in a still larger proportion. The reaction velocity may be controlled by carrying out the reaction under heating or cooling. Commonly, the reaction is advantageously conducted in the temperature range of about −20° to about 100° C.

As the result of the aforementioned acylation reaction, the corresponding acyl group is introduced into the 2-amino group of the compound (III) wherein X is >C=O to yield an imino compound. In this connection, when $Z^1$ or/and $Z^2$ in the compound (III) are hydrogen, there may be produced a compound having the corresponding acyl groups instead of these hydrogen as well depending upon the conditions of acylation reaction. Alternatively $Z^1$ or/and $Z^2$ may be substituted with a protective group before the acylation reaction. As the protective group, any group can be used which is able to protect hydroxy group from the above acylation reaction insofar as it is readily removed. Examples of such protective group include an aralkyl group (e.g. benzyl, α-methylbenzyl, etc.), and so on.

Referring to the compound of the formula (VI), Y is halogen (e.g. chlorine, bromine, iodine, fluorine, etc.) or a substituted sulfonyloxy group (e.g. methanesulfonyloxy, benzenesulfonyloxy, p-toluenesulfonyloxy, p-bromobenzenesulfonyloxy, etc.). The reaction with said compound (VI) is generally conducted in water, an organic solvent or a mixture thereof. As for the organic solvent, use may be made of any organic solvent that will not interfere with the reaction; thus, methanol, ethanol, acetone, chloroform, benzene, ethyl ether, tetrahydrofuran, dioxane, etc. may be mentioned by way of example. For the purpose of hastening the reaction, a base such as sodium hydroxide, sodium carbonate, potassium hydroxide, potassium carbonate, sodium hydrogen carbonate, pyridine, picoline, triethylamine, sodium hydride, sodium alcoholate, t-butoxy potassium or the like may be added as an acid acceptor. The addition of an antioxidant such as ascorbic acid, hydroquinone or the like, or/and the use of an inert gaseous reaction atmosphere such as, for example, nitrogen, helium or argon for the purpose of inhibiting possible side reaction due to oxidation, may in certain circumstances prove conducive to improved yields. The reaction proceeds satisfactorily enough at room temperature but it may be conducted under appropriate heating or cooling in order to control the reaction velocity. It is generally advantageous to carry out the reaction at a temperature from −20° to 100° C. The resulting compound (VII) may be first isolated from the reaction mixture by a conventional isolation and purification procedure, e.g. concentration, distillation, filtration, recrystallization, chromatography or/and the like, and, then, subjected to the hydrolysis reaction mentioned below. Alternatively, the said reaction mixture as such may be used in the hydrolysis reaction.

The hydrolysis reaction in the above reaction formulas is carried out generally by permitting water, an acid or a base to act upon the compound of the formula (VII) in the presence of water or/and an organic solvent. The said acid may for example be an inorganic acid, e.g. hydrochloric acid, hydrobromic acid, hydroiodic acid, sulfuric acid, nitric acid, phosphoric acid or the like; an organic acid such as formic acid, acetic acid or the like; or a Lewis acid such as aluminum chloride, ferric chloride, zinc chloride, boron trifluoride, boron trichloride or the like. The base may for example be an inorganic base such as potassium hydroxide, sodium hydroxide, sodium carbonate, sodium hydrogen carbonate or the like; or an organic base such as pyridine, dimethylaniline, triethylamine or the like. As said organic solvent, use may be made of any organic solvent that does not interfere with the reaction, such as methanol, ethanol, acetone, chloroform, benzene, ethyl ether, tetrahydrofuran, dioxane or the like. While the present hydrolysis reaction proceeds satisfactorily at room temperature, the reaction may be conducted at an appropriately elevated or reduced temperature for the purpose of controlling the reaction velocity. The temperature range which is ordinarily employed is from about 0° to 150° C.

In the case when $Z^3$ and/or $Z^4$ are the acyl group introduced by the aforementioned acylation reaction, or when $Z^3$ and/or $Z^4$ are protective groups introduced before the acylation reaction, they may be eliminated simultaneously during this hydrolysis reaction. If, however, these groups remain unchanged, they may be removed by per se conventional methods.

The resulting compound, i.e. the compound (II) wherein X is >C=O and Q is —NHR$^1$ can be easily isolated from the reaction mixture by separation and purification procedures which are known per se, such as concentration, distillation, filtration, recrystallization, chromatography and so on.

The reaction (b) is carried out in the presence of the carbonyl compound (IV) under reductive conditions.

These reductive conditions may be attained by the aforementioned reduction reactions in the method of the present invention, advantageously, for example, by reduction with lithium cyanoborohydride or by catalytic reduction employing palladium-on-carbon as the catalyst in the alcoholic solvents. Furthermore, it is feasible to carry out the reaction using an excess of the carbonyl compound (IV) in place of the solvent. While the effective reaction temperature varies with reduction procedures that may be selected, it is usually advantageous to conduct the reaction within the temperature range of about −20° to 100° C. The present reaction is ordinarily carried out at atmospheric pressure but, if desired, may be conducted at reduced or elevated pressure.

The resulting compound, i.e. the compound (II) wherein X is >C=O and Q is —NHR¹ can be easily isolated from the reaction mixture by conventional separation and purification procedures such as concentration, distillation, recrystallization, column chromatography and so on.

The compound (II) thus obtained by the reaction (a) or (b) may also be isolated in the form of a salt, for example an acid addition salt with an inorganic acid, e.g. hydrochloric acid, hydrobromic acid, sulfuric acid, nitric acid, phosphoric acid or the like, or with an organic acid, e.g. acetic acid, fumaric acid, maleic acid, tartric acid, malic acid or the like.

The starting compound (II) wherein X is >C=O and Q is —NHR¹ described in detail hereinbefore, inclusive of the acid addition salt thereof, has also sympathetic nerve stimulant or blocking activities and can be used in the prophylaxis and therapy of asthma or arrhythmia. When these compounds are used as drugs, they may be administered in such oral dosage forms as tablets, capsules, powders, suspensions, syrups, etc. or in such other forms as parenteral injections, inhalations and so on. While the dosage depends upon the symptoms to be ameliorated, the route and manner of administration, etc., the recommended oral dose level for the therapy of asthma, for instance is ordinarily about 0.1 to 100 milligrams daily per adult human.

The trans- or cis-isomer of the compound (III) wherein X is >CH—OH which may be employed to produce the corresponding trans- or cis-isomer of the compound (I) can each be obtained, for example, according to the following reaction formulas.

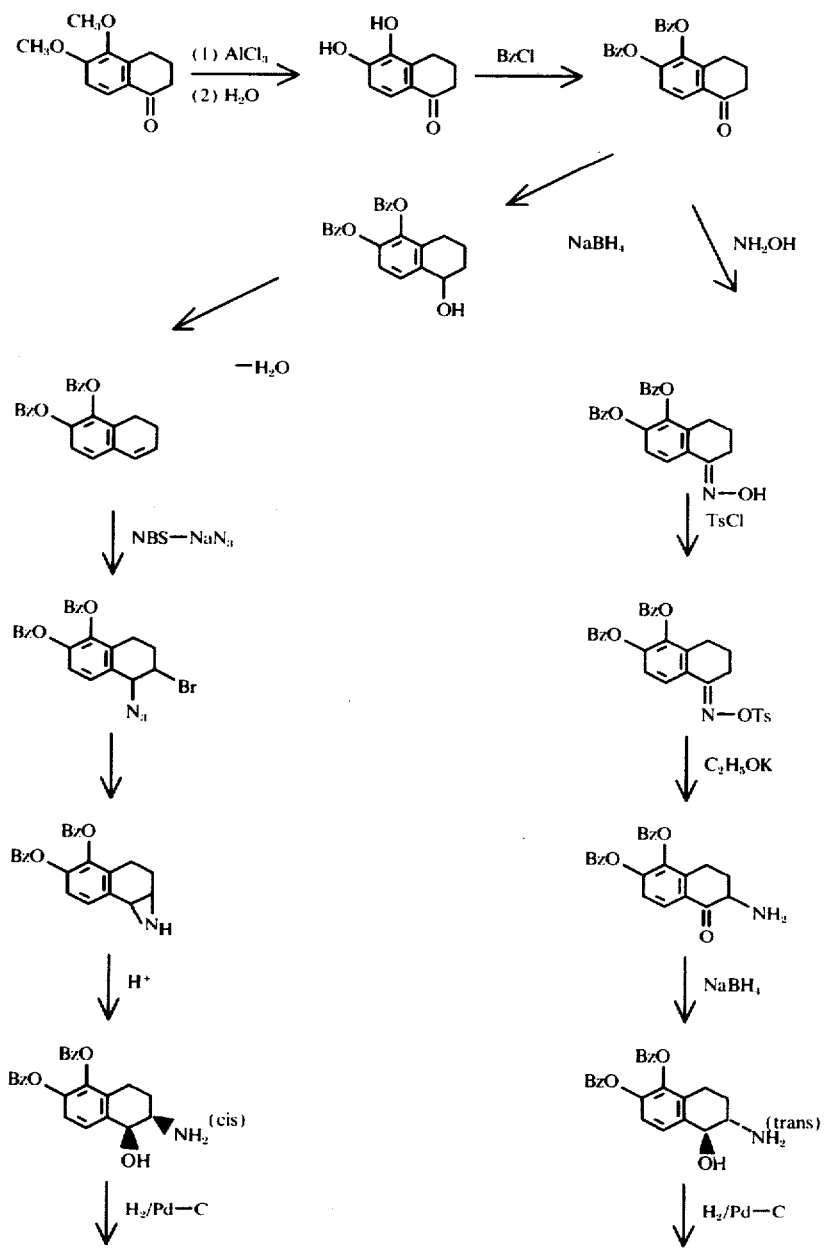

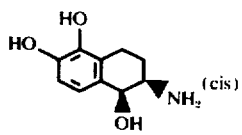

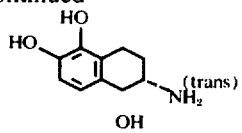

(wherein Bz is —CH$_2$—⟨⟩, Ts is —SO$_2$—⟨⟩—CH$_3$ and NBS is N-bromosuccinimide).

(wherein Bz is

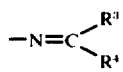

and NBS is N-bromosuccinimide).

It is possible to obtain the trans- or cis-isomer of the compound (I) via the compound (II) wherein X is >CH—OH and Q is

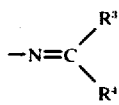

by employing the corresponding isomer of the compound (III) wherein X is >CH—OH in the reaction with the carbonyl compound (IV).

The aforementioned starting compound (II) and the compound (III) may each be employed in the free form or may also be used for the method of this invention as acid addition salts such as inorganic acid salts (e.g. hydrochloride, hydrobromide, sulfate, etc.) and organic acid salts (e.g. maleate, fumarate, tartrate, toluenesulfonate, naphthalenesulfonate, methanesulfonate, etc.), for instance.

The following Reference Examples and Examples are further illustrative of this invention. It should, of course, be understood that the scope of the invention is by no means limited by and to these examples.

In the following Reference Examples and Examples, the word "part(s)" is based on weight unless otherwise noted and relationship between "part(s)" and "volume part(s)" corresponds to that between "gram(s)" and "milliliter(s)".

REFERENCE EXAMPLE 1

30 parts of 2-amino-5,6-dimethoxy-3,4-dihydro-1(2H)-naphthalenone hydrochloride is subjected to boiling reflux in 500 volume parts of a 47% aqueous solution of hydrogen bromide for 3 hours and, then, concentrated to dryness under reduced pressure. The residue is dissolved in methanol, followed by the addition of ethyl acetate, whereupon crystals separate. Filtrative recovery yields 31 parts of 2-amino-5,6-dihydroxy-3,4-dihydro-1(2H)-naphthalenone hydrobromide.

This crystalline product shows no definite melting point but decomposes gradually with blackish discoloration at temperatures exceeding 250° C. Infrared absorption spectrum $\gamma_{max}^{KBr}$ cm$^{-1}$: 3500–2800, 1660, 1605, 1580, 1490, 1380, 1310, 1280, 1025, 905, 820.

REFERENCE EXAMPLE 2

In 50 volume parts of water is dissolved 2 parts of 2-amino-5,6-dihydroxy-3,4-dihydro-1(2H)-naphthalenone hydrobromide, and catalytic reduction is carried out using 0.5 part of platinum oxide at ordinary temperature and pressure. The catalyst is filtered off and a solvent mixture of ethyl ether and methanol is added dropwise to the filtrate, whereupon 2-amino-1,5,6-trihydroxy-1,2,3,4-tetrahydronaphthalene hydrobromide is obtained as colorless prisms. Yield 1 part; melting point: 190°–200° C (decomposition).

Elemental analysis: for $C_{10}H_{13}O_3N \cdot HBr \cdot H_2O$. Calculated: C, 40.84, H, 5.48; N, 4.76. Found: C, 40.49; H, 5.37; N, 4.61.

REFERENCE EXAMPLE 3

In a mixture of 200 volume parts of dry methanol and 200 volume parts of cyclohexanone is dissolved 10 parts of 2-amino-5,6-dimethoxy-3,4-dihydro-1(2H)-naphthalenone hydrochloride and under nitrogen sparging and cooling at 0° C, there is added 9 parts of a molecular compound consisting of 1 mole lithium cyanoborohydride and 2 moles dioxane (LiBH$_3$CN·2C$_4$H$_8$O$_2$). At a constant temperature of 5° C, the reaction mixture is stirred for 2 hours. After the addition of dilute hydrochloric acid, the methanol is distilled off. The remaining mixture is washed with benzene and evaporated to dryness under reduced pressure. The residue is dissolved in ethanol, treated with activated carbon and recrystallized from a mixture of ethanol and ethyl ether. The procedure yields 9.65 parts of 2-cyclohexylamino-5,6-dimethoxy-3,4-dihydro-1(2H)-naphthalenone hydrochloride as colorless crystals melting at 180°–190° C (decomposition).

Elemental analysis: for $C_{18}H_{25}O_3N \cdot HCl$. Calculated: C, 63.61; H, 7.71; N, 4.12. Found: C, 63.50; H, 7.46; N, 4.22.

REFERENCE EXAMPLE 4

In a mixture of 50 volume parts 48% hydrobromic acid and 15 volume parts acetic anhydride is dissolved 5 parts of 2-cyclohexylamino-5,6-dimethoxy-3,4-dihydro-1(2H)-naphthalenone hydrochloride, and the solution is heated at 140°–160° C for about 3 hours. After cooling, the solvent is removed under reduced pressure and the residue is treated with activated carbon in ethanol. Following the addition of ethyl acetate, the filtrate is allowed to stand, whereby 2-cyclohexylamino-5,6-dihydroxy-3,4-dihydro-1(2H)-naphthalenone hydrobromide is obtained as colorless prisms. Yield 4.1 parts; melting point: 225°–237° C (decomposition).

Nuclear magnetic resonance spectrum: δ (DMSO-d$_6$): 6.91(1H,d,J=8.4), 7.43(1H,d,J=8.4).

REFERENCE EXAMPLE 5

In a manner similar to that of Reference Example 3, 10 parts of 2-amino-5,6-dimethoxy-3,4-dihydro-1(2H)-naphthalenone hydrochloride is reacted with 300 volume parts of cyclopentanone. The procedure yields 10.2 parts of 2-cyclopentylamino-5,6-dimethoxy-3,4-dihydro-1(2H)-naphthalenone hydrochloride as colorless crystals melting at 158°–167° C (decomposition).

Elemental analysis: for $C_{17}H_{23}O_3N \cdot HCl$. Calculated: C, 62.67; H, 7.42; N, 4.30. Found: C, 62.91; H, 7.15; N, 4.35.

REFERENCE EXAMPLE 6

In a manner similar to that of Reference Example 3, 10.5 parts of 2-amino-5,6-dimethoxy-3,4-dihydro-1(2H)-naphthalenone hydrochloride is reacted with 10 volume parts of cyclobutanone. The procedure yields 8.2 parts of 2-cyclobutylamino-5,6-dimethoxy-3,4-dihydro-1(2H)-naphthalenone hydrochloride. Melting point: 146°–164° C (decomposition).

Elemental analysis: for $C_{16}H_{21}O_3N \cdot HCl \cdot 1/4H_2O$. Calculated: C, 60.76; H, 7.17; N, 4.43. Found: C, 60.78; H, 7.26; N, 4.29.

REFERENCE EXAMPLE 7

In a manner similar to that of Reference Example 4, 5.16 parts of 2-cyclobutylamino-5,6-dimethoxy-3,4-dihydro-1(2H)-naphthalenone hydrochloride is hydrolyzed in a mixture of 75 volume parts 48% hydrobromic acid and 15 volume parts acetic anhydride. The procedure yields 4 parts of 2-cyclobutylamino-5,6-dihydroxy-3,4-dihydro-1(2H)-naphthalenone hydrobromide. Melting point: 229°–240° C (decomposition).

Elemental analysis: for $C_{14}H_{17}O_3N \cdot HBr \cdot \frac{1}{2}H_2O$. Calculated: C, 49.86; H, 5.68; N, 4.15. Found: C, 50.10; H, 5.58; N, 4.12.

REFERENCE EXAMPLE 8

In 300 volume parts of ethanol is dissolved 5 parts of 2-amino-5,6-dihydroxy-3,4-dihydro-1(2H)-naphthalenone hydrobromide and, after the addition of 50 parts of β-phenylpropionaldehyde, catalytic reduction is carried out at ordinary temperature and pressure using palladium-on-carbon as a catalyst. When a stoichiometric amount of hydrogen has been absorbed, the reaction mixture is filtered and the filtrate is concentrated under reduced pressure. The procedure yields 3.5 parts of 2-(3-phenylpropyl)amino-5,6-dihydroxy-3,4-dihydro-1(2H)-naphthalenone hydrobromide as colorless crystals melting at 215°–217° C.

Elemental analysis, for $C_{19}H_{21}O_3N \cdot HBr$. Calculated: C, 58.17; H, 5.65; N, 3.57. Found: C, 58.39; H, 5.69; N, 3.18.

REFERENCE EXAMPLE 9

In 1000 volume parts of ethanol is dissolved 10 parts of 2-amino-5,6-dihydroxy-3,4-dihydro-1(2H)-naphthalenone hydrobromide, followed by the addition of 100 parts of 4-methoxyphenylacetaldehyde. Using palladium-on-carbon as a catalyst, catalytic reduction is carried out at ordinary temperature and pressure. When a stoichiometric amount of hydrogen has been absorbed, the reaction mixture is filtered and the filtrate is concentrated under reduced pressure. The procedure yields 8 parts of 2-(4-methoxyphenethyl)amino-5,6-dihydroxy-3,4-dihydro-1(2H)-naphthalenone hydrobromide as colorless crystals melting at 198°–203° C.

Elemental analysis, for $C_{19}H_{21}O_4N \cdot HBr$. Calculated: C, 55.89; H, 5.43; N, 3.43. Found: C, 56.30; H, 5.38; N, 3.05.

REFERENCE EXAMPLE 10

To 500 parts of trifluoroacetic anhydride is added 20 parts of 2-amino-5,6-dimethoxy-3,4-dihydro-1(2H)-naphthalenone hydrochloride. The mixture is allowed to stand at room temperature for 30 minutes, after which time a small amount of ethyl ether and 1000 volume parts of n-hexane are added. The resultant crystals are recovered by filtration. The foregoing procedure yields 24 parts of 2-trifluoroacetamido-5,6-dimethoxy-3,4-dihydro-1(2H)-naphthalenone melting at 166°–167° C.

Elemental analysis, for $C_{14}H_{14}O_4NF_3$. Calculated: C, 52.98; H, 4.45; N, 4.42. Found: C, 52.54; H, 4.38; N, 4.14.

15 Parts of the above product is dissolved in 1500 volume parts of acetone previously saturated with nitrogen gas, followed by the addition of 50 parts of potassium carbonate and 30 parts of 4-methoxyphenethyl bromide. The mixture is stirred in nitrogen streams for 2 days. The resultant product is boiled on reflux for 3 hours in 200 volume parts of a 47% aqueous solution of hydrogen bromide.

The reaction product is extracted with ethyl acetate and the water layer is filtered with the addition of a small amount of activated carbon. The filtrate is concentrated under reduced pressure and at a temperature not exceeding 50° C. The residue is dissolved in methanol and to the solution is added ethyl ether dropwise until white turbidity appears. The mixture is allowed to stand in the cold for a week and the resultant crystals are recovered by filtration. The procedure yields 3 parts of 5,6-dihydroxy-2-(4-methoxyphenethylamino)-3,4-dihydro-1(2H)-naphthalenone hydrobromide melting at 198°–203° C (decomposition).

Elemental analysis, for $C_{19}H_{21}O_4N \cdot HBr$. Calculated: C, 55.89; H, 5.43; N, 3.43. Found: C, 56.51; H, 5.30; N, 3.17.

REFERENCE EXAMPLE 11

To 500 parts of trifluoroacetic anhydride is added 20 parts of 2-amino-5,6-methylenedioxy-3,4-dihydro-1(2H)-naphthalenone hydrochloride and after a standing period of 30 minutes at room temperature, 1000 volume parts of n-hexane is added. The supernatant fluid is decanted off and the precipitated 2-trifluoroacetamido-5,6-methylenedioxy-3,4-dihydro-1(2H)-naphthalenone is dissolved in 2500 volume parts of acetone saturated with nitrogen gas. Following the addition of 80 parts of potassium carbonate and 60 parts of cyclohexanol p-toluenesulfonic acid ester, the solution is stirred in nitrogen streams for 7 days. The insolubles are filtered off and the filtrate is distilled under reduced pressure to recover a crude product of 2-(N-cyclohexyl-N-trifluoroacetamido)-5,6-methylenedioxy-3,4-dihydro-1(2H)-naphthalenone. This product is added to 800 volume parts of a 47% aqueous solution of hydrogen bromide and the mixture is boiled on reflux for 3 hours. After cooling, the reaction mixture is extracted with ethyl acetate. To the water layer are added a small amount of activated carbon and 500 volume parts of methanol saturated with nitrogen gas, followed by filtration. The filtrate is evaporated to dryness under reduced pressure and the residue is dissolved in methanol. The white turbid solution obtained by the dropwise addition of ethyl ether, is allowed to stand in a refrigerator for 2 weeks and the resultant crystals are recovered by filtration. The procedure yields 2 parts of 2-cyclohexylamino5,6-dihydroxy-3,4-dihydro-1(2H)-naphthalenone hydrobromide melting at 225°–237° C (decomposition).

Elemental analysis, for $C_{16}H_{21}O_3N \cdot HBr$. Calculated: C, 53.94; H, 6. ; N, 3.93. Found: C, 53.67; H, 6.22; N, 3.79.

Mass spectrum (m/e): 275(M$^+$).

REFERENCE EXAMPLE 12

20 Parts of 2-amino-5,6-dibenzyloxy-3,4-dihydro-1(2H)-naphthalenone hydrochloride is subjected to a procedure similar to that described in Reference Example 11 and the resultant 5,6-dibenzyloxy-2-trifluoroacetamido-3,4-dihydro-1(2H)-naphthalenone is reacted with 60 parts of 3-phenylpropanol p-toluenesulfonic acid ester under the same conditions as set forth in Reference Example 11. The reaction product is then hydrolyzed in a 47% aqueous solution of hydrogen bromide to obtain 3 parts of 5,6-dihydroxy-2-(3-phenylpropylamino)-3,4-dihydro-1(2H)-naphthalenone hydrobromide melting at 215°–217° C (decomposition).

Elemental analysis, for $C_{19}H_{21}O_3N \cdot NBr$. Calculated: C, 58.17; H, 5.65; N, 3.57. Found: C, 58.00; H, 5.17; N, 3.25.

EXAMPLE 1

In 200 volume parts of ethanol is dissolved 2 parts of 2-amino-1,5,6-trihydroxy-1,2,3,4-tetrahydronaphthalene hydrobromide, followed by the addition of 20 parts of β-phenylpropionaldehyde to produce 2-(3-phenylpropylideneamino)-1,5,6-trihydroxy-1,2,3,4-tetrahydronaphthalene. Using palladium-on-carbon as a catalyst, the reaction mixture is subjected to catalytic reduction at ordinary temperature and pressure. After a stoichiometric amount of hydrogen has been absorbed, the reaction mixture is filtered to remove the catalyst and, then, 5000 volume parts of ethyl ether is added to the filtrate. The procedure yields 2 parts of 2-(3-phenylpropylamino)-1,5,6-trihydroxy-1,2,3,4-tetrahydronaphthalene hydrobromide as white crystals melting at 136°–139° C (decomposition).

Elemental analysis: for $C_{19}H_{23}O_3N \cdot HBr \cdot \frac{1}{2}H_2O$. Calculated: C, 56.58; H, 6.25; N, 13.47. Found: C, 56.60; H, 5.89; N, 3.25.

EXAMPLE 2–7

In manners similar to that of Example 1, the products listed in Table 2 are obtained via corresponding intermediates by reacting 2-amino-1,5,6-trihydroxy-1,2,3,4-tetrahydronaphthalene hydrobromide with corresponding carbonyl compounds indicated in Table 2.

Table 2

Product: 5,6-dihydroxy-1-hydroxy-tetrahydronaphthalene-NHR·HBr

| Example | Carbonyl compound | R | Solvent for recrystallization | Melting point (Decomposition) (°C) | Elemental analysis Molecular formula Calculated (Found) |
|---|---|---|---|---|---|
| 2 | phenylacetaldehyde | —(CH$_2$)$_2$—C$_6$H$_5$ | ethanol-ether | 146–149 | $C_{18}H_{21}O_3N \cdot HBr \cdot H_2O$<br>C 54.26, H 6.07, N 3.52<br>(C 54.64, H 6.04, N 3.16) |
| 3 | 4-methoxyphenylacetaldehyde | —(CH$_2$)$_2$—C$_6$H$_4$—OCH$_3$ | ethanol-ether | 138–140 | $C_{19}H_{23}O_4N \cdot HBr \cdot H_2O$<br>C 53.28, H 6.12, N 3.27<br>(C 53.60, H 5.75, N 3.24) |
| 4 | α-phenylpropionaldehyde | —CH$_2$CH(CH$_3$)—C$_6$H$_5$ | ethanol-ether | 149–151 | $C_{19}H_{23}O_3N \cdot HBr \cdot H_2O$<br>C 55.33, H 6.35, N 3.40<br>(C 55.77, H 5.80, N 3.51) |
| 5 | tetrahydropyran-2-carbaldehyde | —CH$_2$—(tetrahydropyranyl) | ethanol-ether | 155–158 | $C_{16}H_{23}O_4N \cdot HBr \cdot H_2O$<br>C 49.98, H 6.68, N 3.57<br>(C 49.20, H 6.49, N 3.54) |
| 6 | cyclohexanecarbaldehyde | —CH$_2$—C$_6$H$_{11}$ | ethanol-ether | 161–164 | $C_{17}H_{25}O_3N \cdot HBr \cdot H_2O$<br>C 52.31, H 7.23, N 3.59<br>(C 52.74, H 7.07, N 3.32) |

Table 2-continued

Product: [structure: HO, HO-naphthalene-tetrahydro with OH and NHR·HBr]

| Example | Carbonyl compound | R | Solvent for recrystallization | Melting point (Decomposition) (°C) | Elemental analysis Molecular formula Calculated (Found) |
|---|---|---|---|---|---|
| 7 | methoxyacetaldehyde | —CH$_2$CH$_2$OCH$_3$ | ethanol | 156–159 | C$_{13}$H$_{19}$O$_4$N . HBr<br>C 46.72, H 6.03, N 4.19<br>(C 46.46, H 5.99, N 4.29) |

EXAMPLE 8

In 200 volume parts of ethanol is dissolved 2 parts of 2-amino-1,5,6-trihydroxy-1,2,3,4-tetrahydronaphthalene hydrobromide, followed by the addition of 20 parts of phenylacetone and 0.7 part of triethylamine. Using palladium-on-carbon as a catalyst, catalytic reduction is carried out at ordinary temperature and pressure. After 24 hours, the reaction mixture is filtered to remove the catalyst and the filtrate is concentrated under reduced pressure at room temperature. To the residue is added an alcoholic solution of 1 part fumaric acid. Then, 50 volume parts of water and 2,000 volume parts of ether are added successively, followed by cooling. The procedure yields 6 parts of trans-2-(α-methylphenethylamino)-1,5,6-trihydroxy-1,2,3,4-tetrahydronaphthalene fumarate as colorless granules melting at 145°–148° C (decomposition).

Elemental analysis: for C$_{19}$H$_{23}$O$_3$N·C$_4$H$_4$O$_4$. Calculated: C, 64.32; H, 6.34; N, 3.26. Found: C, 63.94; H, 6.69; N, 3.51.

Nuclear magnetic resonance spectrum δ (DMSO-d$_6$): 4.54(1H,d,J=9Hz)

EXAMPLE 9

In 300 volume parts of ethanol is dissolved 3 parts of 2-amino-1,5,6-trihydroxy-1,2,3,4-tetrahydronaphthalene hydrobromide and, then, 20 parts of 4-methoxyphenylacetone and 1.5 parts of triethylamine are added. Using palladium-on-carbon as a catalyst, catalytic reduction in hydrogen streams is conducted at ordinary temperature and pressure for 3 days. The reaction mixture is filtered to remove the catalyst and, following the addition of 1.5 parts of fumaric acid, the filtrate is concentrated under reduced pressure. To the residue is added water and the resulting solution is extracted with ethyl ether to remove the solubles.

The water layer is neutralized with an aqueous solution of sodium hydrogen carbonate and extracted three times with chloroform. The chloroform solution of 2-(4-methoxy-α-methylphenethylamino)-1,5,6-trihydroxy-1,2,3,4-tetrahydronaphthalene thus obtained is dried over sodium sulfate and, following the addition of 1.5 parts fumaric acid, concentrated under reduced pressure. The residue is recrystallized from ethanol. The procedure yields 1 part of trans-2-(4-methoxy-α-methylphenethylamino)-1,5,6-trihydroxy-1,2,3,4-tetrahydronaphthalene fumarate as colorless crystals melting at 150°–153° C (decomposition).

Elemental analysis: for C$_{20}$H$_{25}$O$_4$N·C$_4$H$_4$O$_4$. Calculated: C, 62.73; H, 6.36; N, 3.05. Found: C, 63.17; H, 6.59; N, 3.10.

Nuclear magnetic resonance spectrum δ (DMSO-d$_6$): 4.60(1H,d,J=9Hz)

EXAMPLE 10

Using 1.91 parts of 5 % palladium-on-carbon, 1.89 parts of 2-cyclohexylamino-5,6-dihydroxy-3,4-dihydro-1(2H)-naphthalenone hydrobromide in 50 volume parts of water is subjected to catalytic reduction at ordinary temperature and pressure. When a stoichiometric amount of hydrogen has been absorbed, the reaction mixture is filtered to remove the catalyst and the filtrate is freeze-dried. The residue is recrystallized from a mixture of ethanol and ethyl acetate, whereby 2-cyclohexylamino-1,5,6-trihydroxy-1,2,3,4-tetrahydronaphthalene hydrobromide is obtained as colorless crystals. Yield 1.38 parts; melting point: 230°–236° C (decomposition).

Nuclear magnetic resonance spectrum δ (DMSO-d$_6$+D$_2$O): 4.56 –4.80(1H,m), 6.40–6.70(2H,m).

EXAMPLE 11

Using 2 parts of 5 % palladium-on-carbon, 2 parts of 2-cyclopentylamino-5,6-dihydroxy-3,4-dihydro-1(2H)-naphthalenone hydrobromide in 50 volume parts of water is subjected to catalytic reduction at ordinary temperature and pressure. After a stoichiometric amount of hydrogen has been absorbed, the reaction is terminated and the catalyst is filtered off. The filtrate is freeze-dried and the residue is recrystallized from a mixture of ethanol and ethyl acetate. The procedure yields 1.54 parts of 2-cyclopentylamino-1,5,6-trihydroxy-1,2,3,4-tetrahydronaphthalene hydrobromide as colorless crystals melting at 210°–218° C (decomposition).

Mass spectrum: m/e: 263(M$^+$).

Nuclear magnetic resonance spectrum: δ (DMSO-d$_6$+D$_2$O): 4.62(1H,d,J=8Hz), 6.60–6.90(2H,m).

EXAMPLES 12 to 21

In manners similar to that of Example 10 or 11, the products listed in the table below are obtained by catalytic reduction of the corresponding 3,4-dihydro-2-substituted amino-5,6-dihydroxy-1(2H)-naphthalenone hydrobromides.

Table 3

Product:

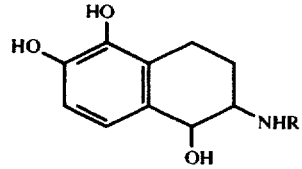

| Example | R | Salt | Melting point (decomp.) |
|---|---|---|---|
| 12 | —(CH$_2$)$_3$—C$_6$H$_5$ | Hydrobromide | 136–139 |
| 13 | —(CH$_2$)$_2$—C$_6$H$_5$ | Hydrobromide | 146–149 |
| 14 | —(CH$_2$)$_2$—C$_6$H$_4$—OCH$_3$ | Hydrobromide | 138–140 |
| 15 | —CH$_2$CH(CH$_3$)—C$_6$H$_5$ | Hydrobromide | 149–151 |
| 16 | —CH$_2$-(tetrahydropyranyl) | Hydrobromide | 155–158 |
| 17 | —CH$_2$-cyclohexyl | Hydrobromide | 161–164 |
| 18 | —CH$_2$CH$_2$OCH$_3$ | Hydrobromide | 156–159 |
| 19 | —CH(CH$_3$)—CH$_2$—C$_6$H$_5$ | Fumarate | 145–148 |
| 20 | —CH(CH$_3$)—CH$_2$—C$_6$H$_4$—OCH$_3$ | Fumarate | 150–153 |
| 21 | —CH(CH$_3$)—CH$_2$—C$_6$H$_4$—OH | Fumarate | 137–141 |

EXAMPLE 22

In a mixture of 50 volume parts of cyclohexanone and 200 volume parts of ethanol is dissolved 0.151 part of 2-amino-5,6-dihydroxy-3,4-dihydro-1(2H)-naphthalenone hydrobromide to produce 2-cyclohexylideneamino-5,6-dihydroxy-3,4-dihydro-1(2H)-naphthalenone.

The resulting mixture is subjected to catalytic reduction with 0.16 part platinum dioxide and 0.57 part anhydrous sodium acetate at ordinary temperature and pressure. After a stoichiometric amount of hydrogen has been absorbed, 1 volume part of 48 % hydrobromic acid is added and the catalyst is removed by filtration. The ethanol is removed from the filtrate by distillation and the residue is diluted with water and washed with benzene. The aqueous layer is freeze-dried and the residue is recrystallized from a mixture of ethanol and ethyl acetate. The described procedure yields 2-cyclohexylamino-1,5,6-trihydroxy-1,2,3,4-tetrahydronaphthalene hydrobromide. Melting point: 230°–234° C (decomposition). This product was identified as the compounded according to Example 10.

EXAMPLE 23

In a mixture of 20 volume parts of cyclopentanone and 100 volume parts of ethanol is dissolved 1 part of 2-amino-5,6-dhydroxy-3,4-dihydro-1(2H)-naphthalenone hydrobromide to produce 2-cyclopentylideneamino-5,6-dihydroxy-3,4-dihydro-1(2H)-naphthalenone. The resulting mixture is subjected to catalytic reduction with 0.1 part of platinum dioxide and 0.39 part of anhydrous sodium acetate at ordinary temperature and pressure.

After a stoichiometric amount of hydrogen gas has been absorbed, 1 volume part of 48 % hydrobromic acid is added and the catalyst is filtered off. The ethanol is removed from the filtrate by distillation and the residue is diluted with water and washed with benzene.

The aqueous layer is freeze-dried and the residue is recrystallized from a mixture of ethanol and ethyl acetate.

The procedure yields 0.5 part of 2-cyclopentylamino-1,5,6-trihydroxy-1,2,3,4-tetrahydronaphthalene hydrobromide as colorless crystals melting at 208°–218° C (decomposition). This product was identified as the compound according to Example 11.

EXAMPLE 24

In 100 volume parts of methanol is dissolved 1 part of 2-benzylamino-5,6-dimethoxy-3,4-dihydro-1(2H)-naphthalenone hydrochloride and, under stirring, 2 parts of sodium borohydride is added in small portions. The mixture is stirred at room temperature for 10 minutes, after which time 500 volume parts of water is added. The mixture is then extracted with chloroform. The extract is dried over sodium sulfate and concentrated under reduced pressure.

Finally, the residue is recrystallized from ethyl ether to recover 0.4 part of trans-2-benzylamino-5,6-dimethoxy-1-hydroxy-1,2,3,4-tetrahydronaphthalene as colorless crystals melting at 133°–135° C (decomposition).

Elemental analysis: for $C_{19}H_{23}O_3N$. Calculated: C, 72.82; H, 7.40; N, 4.47. Found: C, 72.42; H, 7.32; N, 4.45.

EXAMPLE 25

To 50 volume parts of tetrahydrofuran are added 1 part of 2-benzoylamino-5,6-dimethoxy-3,4-dihydro-1(2H)-naphthalenone and 0.2 part of lithium aluminum hydride and the mixture is refluxed for 4 hours. The reaction mixture is rendered sufficiently acid with 1N hydrochloric acid and extracted with chloroform to remove non-basic ingredients.

The aqueous layer is made alkaline with 1N aqueous sodium hydroxide and extracted with chloroform. The chloroform solution thus obtained is dehydrated and evaporated to dryness. The residue is recrystallized from ethyl ether to obtain 0.4 part of trans-2-benzylamino-5,6-dimethoxy-1-hydroxy-1,2,3,4-tetrahydronaphthalene as colorless crystals melting at 133°–135° C (decomposition).

The product was identified as the compound of Example 24 by mixed melting point.

EXAMPLE 26

In 200 volume parts of ethanol is dissolved 2 parts of 2-amino-1,5,6-trihydroxy-1,2,3,4-tetrahydronaphthalene hydrobromide, followed by the addition of 20 parts of cinnamaldehyde.

With 5 % palladium-on-carbon as a catalyst, catalytic reduction is carried out at ordinary temperature and pressure until no more hydrogen is absorbed. The catalyst is removed by filtration and 5,000 volume parts of ethyl ether is added to the filtrate. The mixture is allowed to stand and the resulting colorless crystals are recovered by filtration. The procedure yields 1.5 parts of 2-(3-phenylpropylamino)-1,5,6-trihydroxy-1,2,3,4-tetrahydronaphthalene hydrobromide, melting point: 136°–139° C (decomposition).

Elemental analysis: for $C_{19}H_{23}O_3N \cdot HBr \cdot \frac{1}{2}H_2O$. Calculated: C, 56.58; H, 6.25; N, 3.47. Found: C, 56.18; H, 6.18; N, 3.19.

EXAMPLES 27–31

In manners similar to that of Example 26, the products set forth in Table 4 below are synthesized from 2-amino-1,5,6-trihydroxy-1,2,3,4-tetrahydronaphthalene hydrobromide and unsaturated carbonyl compounds.

Table 4

| Example | Unsaturated carbonyl compound | R | Catalyst* | Melting point (decomposition) (° C) |
|---|---|---|---|---|
| 27 | cyclohexanone | -CH₂-phenyl | A | 230–236 |
| 28 | cyclopentanone | -CH₂-phenyl | A | 210–218 |

Table 4-continued

| Example | Unsaturated carbonyl compound | R | Catalyst* | Melting point (decomposition) (°C) |
|---|---|---|---|---|
| 29 | (3,4-dihydro-2H-pyran-2-yl)CHO | —CH$_2$—(tetrahydropyran-2-yl) | A | 155–158 |
| 30 | C$_6$H$_5$—CH$_2$CH$_2$CHO | —(CH$_2$)$_3$—cyclohexyl | B | 160–162 |
| 31 | C$_6$H$_5$—CH$_2$CHO | —(CH$_2$)$_2$—cyclohexyl | B | 168–171 |

*Catalyst A: 5 % palladium-on-carbon
*Catalyst B: Platinum dioxide

EXAMPLE 32

In the presence of 2 parts of 5 % palladium-on-carbon, 2 parts of 2-(3,4-dihydro-2H-pyran-2-yl)methylamino-5,6-dihydroxy-3,4-dihydro-1(2H)-naphthalenone hydrobromide is catalytically reduced in 50 volume parts of water at ordinary temperature and pressure until no more hydrogen is absorbed. The catalyst is filtered off and the filtrate is freeze-dried. The above procedure yields 2 parts of 2-(tetrahydropyran-2-yl)methylamino-1,5,6-trihydroxy-1,2,3,4-tetrahydronaphthalene hydrobromide as colorless crystals melting at 155°–158° C (decomposition). The product was identified as that of Example 5 by mixed melting point)

EXAMPLES 33–34

In manners similar to that of Example 32, the compounds listed in the following table are synthesized.

EXAMPLE 35

In the presence of 1.53 parts of 5 % palladium-on-carbon, 1.5 parts of 2-cyclobutylamino-5,6-dihydroxy-3,4-dihydro-1(2H)-naphthalenone hydrobromide in 200 volume parts of water is subjected to catalytic reduction at ordinary temperature and pressure. When a stoichiometric amount of hydrogen has been absorbed, the reaction mixture is filtered to remove the catalyst and filtrate is freeze-dried. The residue is recrystallized from a mixture of water, ethanol and ethyl ether, whereby 2-cyclobutylamino-1,5,6-trihydroxy-1,2,3,4-tetrahydronaphthalene hydrobromide is obtained as colorless crystals. Yield 0.65 part; melting point: 190°–200° C (decomposition).

Elemental analysis: for $C_{14}H_{19}O_3N \cdot HBr$. Calculated: C, 50.92; H, 6.10; N, 4.24
Found: C, 50.68; H, 5.85; N, 4.05.

Nuclear magnetic resonance spectrum $\delta$ (d$_6$-DMSO+D$_2$O): 4.58(1H,d,J=8Hz), 6.70(1H,d,J=8Hz), 6.84(1H,d,J=8Hz)

Table 5

| Example | Starting compound | Product | Melting point (decomposition) °C |
|---|---|---|---|
| 33 | 5,6-dihydroxy-2-(NHCH$_2$—CH=CH—C$_6$H$_5$)-3,4-dihydro-1(2H)-naphthalenone · HBr | 1,5,6-trihydroxy-2-[NH(CH$_2$)$_3$—C$_6$H$_5$]-1,2,3,4-tetrahydronaphthalene · HBr | 136–139 |
| 34 | 5,6-dihydroxy-2-(NH-cyclohexenyl)-3,4-dihydro-1(2H)-naphthalenone · HBr | 1,5,6-trihydroxy-2-(NH-cyclohexyl)-1,2,3,4-tetrahydronaphthalene · HBr | 230–236 |

Infrared absorption spectrum $\gamma_{max}^{KBr}$ (cm$^{+1}$): 3370, 3120, 2930, 2780, 1620, 1595, 1500, 1295, 1010, 890, 815.

EXAMPLE 36

In a manner similar to that of Example 23, 1 part of 2-amino-5,6-dihydroxy-3,4-dihydro-1(2H)-naphthalenone hydrobromide is reacted with 20 volume parts of cyclobutanone. Via 2-cyclobutylideneamino-5,6-dihydroxy-3,4-dihydro-1(2H)-naphthalenone, 0.5 part of 2-cyclobutylamino-1,5,6-trihydroxy-1,2,3,4-tetrahydronaphthalene hydrobromide is obtained as colorless crystals melting at 190°–200° C (decomposition). This product was identified as the compound according to Example 35 by mixed melting point.

EXAMPLE 37

In a manner similar to that of Example 9, 3 parts of cis-2-amino-1,5,6-trihydroxy-1,2,3,4-tetrahydronaphthalene hydrobromide is reacted with 10 parts of cyclobutanone. Via cis-2-cyclobutylideneamino-1,5,6-trihydroxy-1,2,3,4-tetrahydronaphthalene, 1.0 part of cis-2-cyclobutylamino-1,5,6-trihydroxy-1,2,3,4-tetrahydronaphthalene fumarate is obtained as colorless crystals melting at 171°–172° c (decomposition).

Nuclear magnetic resonance spectrum δ (DMSO-d$_6$+D$_2$O): 4.66(1H,d,J=3Hz).

EXAMPLE 38

In a manner similar to that of Example 9, 3 parts of trans-2-amino-1,5,6-trihydroxy-1,2,3,4-tetrahydronaphthalene hydrobromide is reacted with 10 parts of cyclobutanone. Via trans-2-cyclobutylideneamino-1,5,6-trihydroxy-1,2,3,4-tetrahydronaphthalene, 1.5 parts of trans-2-cyclobutylamino-1,5,6-trihydroxy-1,2,3,4-tetrahydronaphthalene fumarate is obtained as colorless crystals melting at 211°–214° C (decomposition).

Nuclear magnetic resonance spectrum δ (DMSO-d$_6$+D$_2$O): 4.56(1H,d,J=9Hz).

EXAMPLE 39

In a manner similar to that of Example 9, 4 parts of 2-amino-1,5,6-trihydroxy-1,2,3,4-tetrahydronaphthalene hydrobromide is reacted with 20 parts of 3-indolylacetone and, the reaction product is recrystallized from a mixture of ethyl acetate and ether. The procedure yields 1.2 parts of trans-2-[2-(indol-3-yl)-1-methyl]ethylamino-1,5,6-trihydroxy-1,2,3,4-tetrahydronaphthalene fumarate as colorless crystals.

This compound shows no definite melting point and decomposes gradually on heating.

Elemental analysis: for C$_{21}$H$_{24}$O$_3$N$_2$.C$_4$H$_4$O$_4$. Calculated C, 64.09; H, 6.02; N, 5.98. Found C, 64.30; H, 5.98; N, 5.70.

Nuclear magnetic resonance spectrum δ(DMSO-d$_6$+D$_2$O): 4.74(1H,d,J=8Hz).

EXAMPLE 40

In a manner similar to that of Example 9, 4 parts of 2-amino-1,5,6-trihydroxy-1,2,3,4-tetrahydronaphthalene hydrobromide is reacted with 20 parts of 4-hydroxyphenylacetone. The reaction product is dissolved in ethanol and ethyl acetate is added to the solution. The procedure yields 2 parts of 2-(4-hydroxy-α-methylphenethylamino)-1,5,6-trihydroxy-1,2,3,4-tetrahydronaphthalene fumarate as colorless crystals melting at 137°–141° C.

This product showed no depression of melting point on mixing with the compound according to Example 21.

EXAMPLE 41

In a manner similar to that of Example 35, 3.16 parts of 2-cyclopropylamino-5,6-dihydroxy-3,4-dihydro-1(2H)-naphthalenone hydrobromide is subjected to catalytic reduction. The reaction mixture is filtered to remove the catalyst and, following the addition of 0.72 part of triethylamine, the filtrate is concentrated under reduced pressure. To the residue is added 500 volume parts of water and the resulting solution is extracted three times with each 300 volume parts of n-butanol and, following the addition of 2 parts of fumaric acid, the extract is concentrated under reduced pressure. To the residue is added 1000 volume parts of ethyl ether and, the resulting precipitates are collected by filtration to obtain 0.3 part of 2-cyclopropylamino-1,5,6-trihydroxy-1,2,3,4-tetrahydronaphthalene fumarate as colorless powder melting at 155°–160° C (decomposition).

Elemental analysis: for C$_{13}$H$_{17}$O$_3$N.1/2 C$_4$H$_4$O$_4$.H$_2$O. Calculated C, 57.86; H, 6.80; N, 4.50. Found C, 57.48; H, 6.38; N, 4.71.

EXAMPLE 42

Some examples of formulation in which the contemplated products of this invention are utilized, for example, as a bronchodilator are given below:

| A. (Tablet) | |
|---|---|
| (1) 2-cyclopentylamino-1,5,6-trihydroxy-1,2,3,4-tetrahydronaphthalene hydrobromide | 1.5 mg. |
| (2) lactose | 90.0 mg. |
| (3) corn starch | 38.0 mg. |
| (4) magnesium stearate | 0.5 mg. |
| | 130.0 mg. per tablet |

After mixing (1), (2) and 26 mg. of corn starch thoroughly, the mixture is granulated with paste prepared from 7 mg. of corn starch. (4) and the remaining 5 mg. of corn starch are added to the granules and the mixture is compressed into a tablet of 7 mm. in diameter.

| B. (Capsule) | |
|---|---|
| (1) 2-cyclopentylamino-1,5,6-trihydroxy-1,2,3,4-tetrahydronaphthalene hydrobromide | 1.5 mg. |
| (2) lactose | 144.0 mg. |
| (3) microcrystalline cellulose | 70.0 mg. |
| (4) magnesium stearate | 4.5 mg. |
| | 220.0 mg. per capsule |

All ingredients are thoroughly mixed and is filled into a hard gelatin capsule of size No. 3 (described in the Pharmacopoeia of Japan, eight edition).

| C. (Injection) | |
|---|---|
| (1) 2-cyclopentylamino-1,5,6-trihydroxy-1,2,3,4-tetrahydronaphthalene hydrobromide | 0.05 mg. |
| (2) sodium chloride | 9 mg. |
| (3) chlorobutanol | 5 mg. |

-continued

| | |
|---|---|
| (4) sodium bisulfite | 1 mg. |

All ingredients are dissolved in distilled water to make 1.0 ml. of the solution (pH 5.0). The solution is filled into an amber ampoule. The atmosphere in the ampoule is replaced with nitrogen gas. All the processes are conducted under sterile conditions.

| D. (Inhalation) | |
|---|---|
| (1) 2-cyclopentylamino-1,5,6-trihydroxy-1,2,3,4-tetrahydronaphthalene hydrobromide | 0.25 g. |
| (2) glucose | 5 g. |

(1) and (2) are dissolved in sterilized distilled water to make 100.0 ml. of the solution, which is then filtered through a membrane filter having porosity of 0.22 micron.

| E. (Aerosol for inhalation) | |
|---|---|
| (1) 2-cyclopentylamino-1,5,6-trihydroxy-1,2,3,4-tetrahydronaphthalene hydrobromide | 0.25 g. |
| (2) corn oil | 1 g. |
| (3) sorbitan trioleate | 0.5 g. |
| (4) Freon 12-Feon 11(50 W/W %: 50 W/W %) to make a total of 100 g. | |

In the mixture of (2) and (3), (1) is dispersed homogeneously to make the concentrate. The concentrate and the propellant (4) are then packaged into a metal container under elevated pressure.

What is claimed is:

1. A compound of the formula

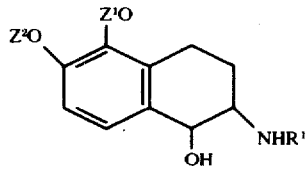

wherein each of $Z^1$ and $Z^2$ is hydrogen or alkyl of 1-6 carbon atoms and $R^1$ is (1) cycloalkyl of 3-7 carbon atoms or (2) alkyl of 1-6 carbon atoms substituted by (a) unsubstituted cycloalkyl of 3-7 carbon atoms, (b) cycloalkyl of 3-7 carbon atoms substituted by alkyl of 1-4 carbon atoms, hydroxyl, alkoxy of 1-4 carbon atoms or halogen, (c) hydroxyl, (d) alkoxy of 1-4 carbon atoms or (e) halogen,
or a pharmaceutically acceptable salt thereof.

2. A compound according to claim 1, which is in the form of a pharmaceutically acceptable salt.

3. A compound according to claim 2, wherein the pharmaceutically acceptable salt is in acid addition salt.

4. A compound according to claim 1, which is in the form of a mixture of trans- and cis-isomers.

5. A compound according to claim 1, which is in the form of a trans-isomer.

6. A compound according to claim 1, wherein $R^1$ is alkyl of 1-6 carbon atoms substituted by (1) unsubstituted cycloalkyl of 3-7 carbon atoms, (2) cycloalkyl of 3-7 carbon atoms substituted as defined in claim 1, or (3) alkoxy of 1-4 carbon atoms.

7. A compound according to claim 1, wherein both $Z^1$ and $Z^2$ are hydrogen.

8. A compound according to claim 1, wherein both $Z^1$ and $Z^2$ are alkyl of 1-6 carbon atoms.

9. A compound according to claim 8, wherein both $Z^1$ and $Z^2$ are methyl.

10. A compound according to claim 1, wherein $R^1$ is alkyl of 1-6 carbon atoms substituted as defined in claim 1.

11. A compound according to claim 1, wherein both $Z^1$ and $Z^2$ are hydrogen and $R^1$ is alkyl of 1-6 carbon atoms substituted as defined in claim 1.

12. A compound according to claim 1, wherein the $R^1$ alkyl of 1-6 carbon atoms is one branching at its α-position.

13. A compound according to claim 1, wherein $R^1$ is cycloalkyl of 3-7 carbon atoms.

14. A compound according to claim 1, wherein both $Z^1$ and $Z^2$ are hydrogen and $R^1$ is cycloalkyl of 3-7 carbon atoms.

15. The compound according to claim 1, which is 2-cyclopentylamino-1,5,6-trihydroxy-1,2,3,4-tetrahydronaphthalene.

16. The compound according to claim 1, which is 2-cyclobutylamino-1,5,6-trihydroxy-1,2,3,4-tetrahydronaphthalene.

17. The compound according to claim 1, which is trans-2-cyclobutylamino-1,5,6-trihydroxy-1,2,3,4-tetrahydronaphthalene.

18. The compound according to 1, which is cis-2-cyclobutylamino-1,5,6-trihydroxy-1,2,3,4-tetrahydronaphthalene.

19. The compound according to claim 1, which is 2-cyclohexylamino-1,5,6-trihydroxy-1,2,3,4-tetrahydronaphthalene.

20. The compound according to claim 1, which is 2-(2-cyclohexylethylamino)-1,5,6-trihydroxy-1,2,3,4-tetrahydronaphthalene.

21. The compound according to claim 1, which is 2-(3-cyclohexylpropylamino)-1,5,6-trihydroxy-1,2,3,4-tetrahydronaphthalene.

22. A pharmaceutical composition having use as a bronchodialator which comprises, as active ingredient, a pharmaceutically effective amount of a compound of the formula

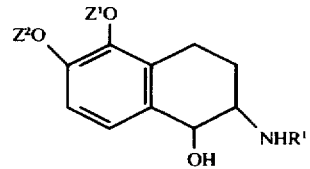

(I)

wherein each of $Z^1$ and $Z^2$ is hydrogen or alkyl of 1-6 carbon atoms and $R^1$ is (1) cycloalkyl of 3-7 carbon atoms or (2) alkyl of 1-6 carbon atoms substituted by (a) unsubstituted cycloalkyl of 3-7 carbon atoms, (b) cycloalkyl of 3-7 carbon atoms substituted by alkyl of 1-4 carbon atoms, hydroxyl, alkoxy of 1-4 carbon atoms or halogen, (c) hydroxyl, (d) alkoxy of 1-4 carbon atoms or (e) halogen,
or a pharmaceutically acceptable salt thereof, together with a pharmaceutically acceptable carrier therefor.

23. A pharmaceutical composition according to claim 22, wherein the compound of formula (I) is in the form of a pharmaceutically acceptable salt.

* * * * *